United States Patent [19]

Couvillion

[11] Patent Number: 4,493,906
[45] Date of Patent: Jan. 15, 1985

[54] CATALYST FOR THE SELECTIVE HYDROGENATION OF ACETYLENES

[75] Inventor: Mark C. Couvillion, Freeport, Tex.

[73] Assignee: The Dow Chemical Company, Midland, Mich.

[21] Appl. No.: 558,128

[22] Filed: Dec. 5, 1983

Related U.S. Application Data

[63] Continuation-in-part of Ser. No. 473,293, Mar. 8, 1983, Pat. No. 4,440,956, which is a continuation-in-part of Ser. No. 436,250, Oct. 25, 1982, abandoned, which is a continuation-in-part of Ser. No. 299,688, Sep. 8, 1981, abandoned.

[51] Int. Cl.³ .......................... B01J 21/04; B01J 23/72
[52] U.S. Cl. .................................. 502/346; 585/260; 585/845
[58] Field of Search ................. 502/346; 585/260, 845

[56] References Cited

U.S. PATENT DOCUMENTS

| | | | |
|---|---|---|---|
| 3,912,789 | 10/1975 | Frevel et al. | 585/260 |
| 4,101,451 | 7/1978 | Frevel et al. | 502/346 |

FOREIGN PATENT DOCUMENTS

| | | | |
|---|---|---|---|
| 1418142 | 2/1970 | Fed. Rep. of Germany | 585/260 |
| 6414578 | 6/1965 | Netherlands | 502/346 |

*Primary Examiner*—W. J. Shine
*Attorney, Agent, or Firm*—G. R. Baker

[57] ABSTRACT

An improved catalyst for removal of acetylenes from liquid hydrocarbon streams with a minimum loss of diolefinic unsaturation present in said liquid composition is disclosed. The catalytic materials, basically copper metal impregnated on a gamma alumina support prepared from an organo aluminum compound. The support has properties not found in alumina prepared from naturally occurring precursors.

3 Claims, 10 Drawing Figures

CATALYST FOR THE SELECTIVE HYDROGENATION OF ACETYLENES

CROSS REFERENCE TO RELATED APPLICATION

This application is a continuation-in-part of my earlier filed application serial no. 473 293, filed Mar. 8, 1983, allowed Sept. 13, 1983, now U.S. Pat. No. 4,440,956, which was a continuation-in-part of application Ser. No. 436,250 filed Oct. 25, 1982, now abandoned, which was a continuation-in-part of application serial no. 299,688 filed Sept. 8, 1981, now abandoned.

BACKGROUND OF THE INVENTION

Copper metal, activated with one or more of the metals silver, platinum, palladium, manganese, cobalt, nickel, chromium and/or molybdenum on an alumina support, is well known as a catalyst for hydrogenation of acetylenes. Frevel et al. have issued several patents in which improved results are obtained (improved selectivity of hydrogenation of the acetylenic bonds in the presence of diolefinic bonding) by increasing the sodium content of the activated catalyst, U.S. Pat. No. 4,101,451, and/or high sodium oxide alumina, U.S. Pat. No. 3,912,789. However, these catalysts still hydrogenate some considerable amount of the diolefin components of such streams. As the diolefin content of these streams becomes more valuable it would be advantageous to reduce the hydrogenation of these diolefins (particularly butadiene) without also reducing the hydrogenation of the α-acetylenes.

BRIEF DESCRIPTION OF THE INVENTION

It has now been found that by employing a gamma alumina which may contain up to 50 percent, preferably 35 percent by weight or less, of alpha alumina and preferably a special grade of gamma alumina ($\gamma$-$Al_2O_3$), one which has low, less than 0.15 weight percent each of silicon as $SiO_2$ and sodium as $Na_2O$, and preferably a soidum content less than about 0.10% less than 0.01 weight percent sulfur and less than 0.06 weight percent iron as $Fe_2O_3$, and additionally has a surface area of between about 68 and 350 square meters per gram and wherein between about 98% and about 40 percent of the pores have a pore diameter between about 40Å and 120Å and not more than 25 percent nor less than 2 percent have a pore diameter between 1000Å to 10,000Å, produces a catalyst support which when coated with about 3 to 13 weight percent copper metal permits reaching lower acetylene levels with less butadiene loss than prior art catalysts and additionally can be effectively regenerated to 90 plus percent activity over several cycles.

It has also been found that during use the gamma alumina described above undergoes a phase change, probably due to thermal treatment during operation and regeneration. Thus, a gamma alumina within the scope above defined will undergo a gradual change, as for example, during a nine month, thirteen cycle (with regeneration) run, to analyze about 35 percent alpha alumina with an attendant reduction in surface area from about 165 square meters per gram to about 68 square meters per gram. There is also a change in the pore volume distribution associated with the reduction in surface area and presence of the alpha alumina. However, the pore sizes remain within the aforedefined range. Thus, while it is preferred to start with a relative high purity gamma alumina having the above described properties and physical characteristics, it is to be understood that a carrier or support may be a combined unitary alumina consisting of a high purity alumina as above defined but having up to fifty percent alpha alumina in admixture with gamma alumina. Such a support can be readily obtained by thermal treatment of gamma alumina of the requisite purity in the presence of cuprous oxide. The phase change apparently occurs as a result of the oxidation and/or reduction during use and regeneration. Presumably the cuprous oxide acts as a seed to effectuate the phase change from gamma to alpha state. However, no specific theory based on scientific data of how such a change occurs can yet be set forth. While the aforestated procedure appears to effect the change, other methods may be available from those skilled in the art of alumina production.

The catalyst carrier or support which appears to be critical or at least preferred to obtaining the aforesaid results is a special grade of gamma alumina ($\gamma$-$Al_2O_3$) prepared by decomposing trialkyl alumina to alpha aluminum monohydrate then calcining the alpha aluminum monohydrate to gamma alumina. This process produces a grade of gamma alumina normally not obtainable from naturally occuring aluminum containing ores and which has, when pressed or extruded into pellets, a higher purity than naturally occurring alumina, and a pore size and pore size distribution sufficiently different from that obtainable using naturally occurring aluminas and converting them to gamma alumina. The most ready source of catalyst support size pellets is from The Harshaw Chemicals Co. sold as 3438T, Norton Company as SA6173 and Calcicat Division, Mallinckrodt Chemical Works as CALCICAT Type A and AA. Although Conoco Chemicals Division, Conoco, Inc., manufactures a powder, CATAPAL type SB which has been found suitable and is believed to be the precursor powder for the three pellet producers, pellets produced by Conoco are not readily available except through the three pelletizers.

DETAILED DESCRIPTION OF THE INVENTION

Example 1

In accordance with the present invention 400 grams of $\gamma$-$Al_2O_3$ of Norton SA6173 obtained from Norton Chemioal Company, as 1/16" diameter extrudates about ¼" long had the following properties:

| | |
|---|---|
| x-ray diffraction pattern matches Joint Committee on Powder Diffraction standards #29-63 | |
| % Na$_2$O | 0.015 |
| % SiO$_2$ | — |
| % Fe$_2$O$_3$ | 0.006 |
| Surface area (m$^2$/g) | 240 |
| Pore volume (cc/g) | 0.56 |
| Bulk density (g/cc) | 0.69 |
| 75% of its pores were less than 75Å | |
| 82% of its pores were less than 100Å | |
| 18% of the pores were between 102Å and 8390Å | |

The unburdened support was impregnated with a solution consisting of:

| | |
|---|---|
| Cu(NO$_3$)$_2$.2½H$_2$O | 140 g |
| H$_2$O | ~40 g |

The resulting solution was poured over 400 grams of the support in a beaker while stirring to obtain even distribution. When all of the solution had been sorbed, the support was dried over night at about 110° C., then calcined at 400° C. for about 6 hours.

The catalyst was loaded to a depth of about 12 inches at the middle of a laboratory 1 inch diameter by 36 inch long reactor. The remaining space of the reactor, above and below the catalyst, was filled with raschig rings. The catalyst was reduced over night with hydrogen in nitrogen at between 300° to 350° C. In the morning the temperature recording from several thermocouples in the bed showed an exotherm had passed up the column during the night signifying reduction of the metal oxides to their metal state. The reactor was cooled to ambient temperature and hydrogen and a liquid hydrocarbon stream having about 61% by weight 1,3-butadiene and 8716 ppm acetylenes was fed to the reactor. The reactor conditions were:

| | |
|---|---|
| Feed | 300 cc/hour |
| Recycle | 600 cc/hour |
| H$_2$ Flow | 2.6 liters/hr at atm. STP |
| H$_2$:C≡ ratio | 3:1 |
| Inlet temperature of liquid | 68° C. |
| T at thermocouple | #1 ca. 68–74° C. |
| | #2 ca. 66–71° C. |
| | #3 ca. 65–69° C. |
| | #4 ca. 60–65° C. |
| | #5 ca. 58–64° C. |

Figure 1:
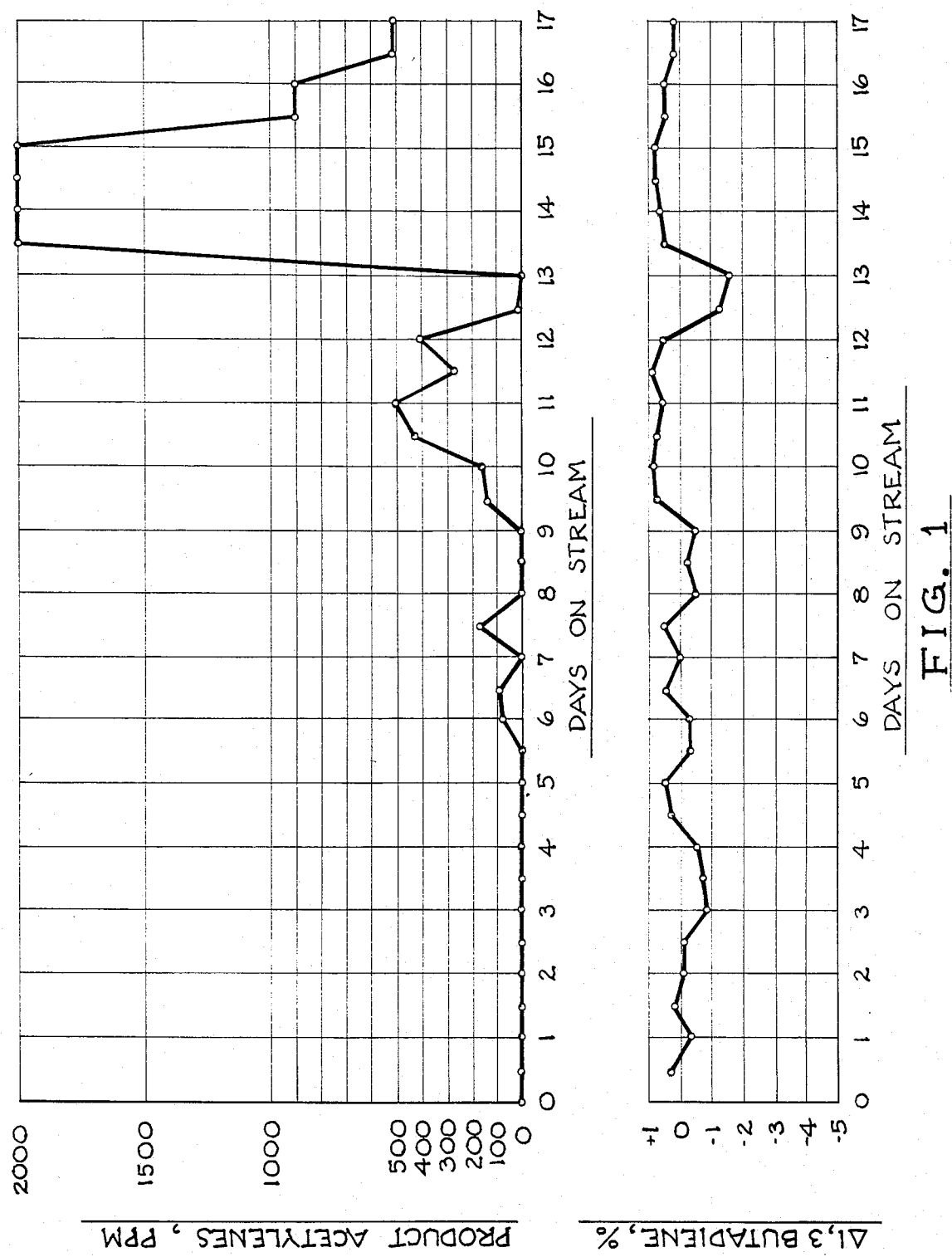
FIG. 1, illustrates the results of an experiment employing a support within the scope of the present invention as a carrier for the catalytically active copper component, with respect to the acetylenes in the product stream and the loss of 1,3-butadiene from the feed stream as a result of the process.

The results of the run is illustrated in FIG. 1 which shows that the product had a 0 ppm acetylenes for the first 5½ days, having less than 0.8% total butadiene loss based on the butadiene present in the feed.

Example 2

Figure 2:
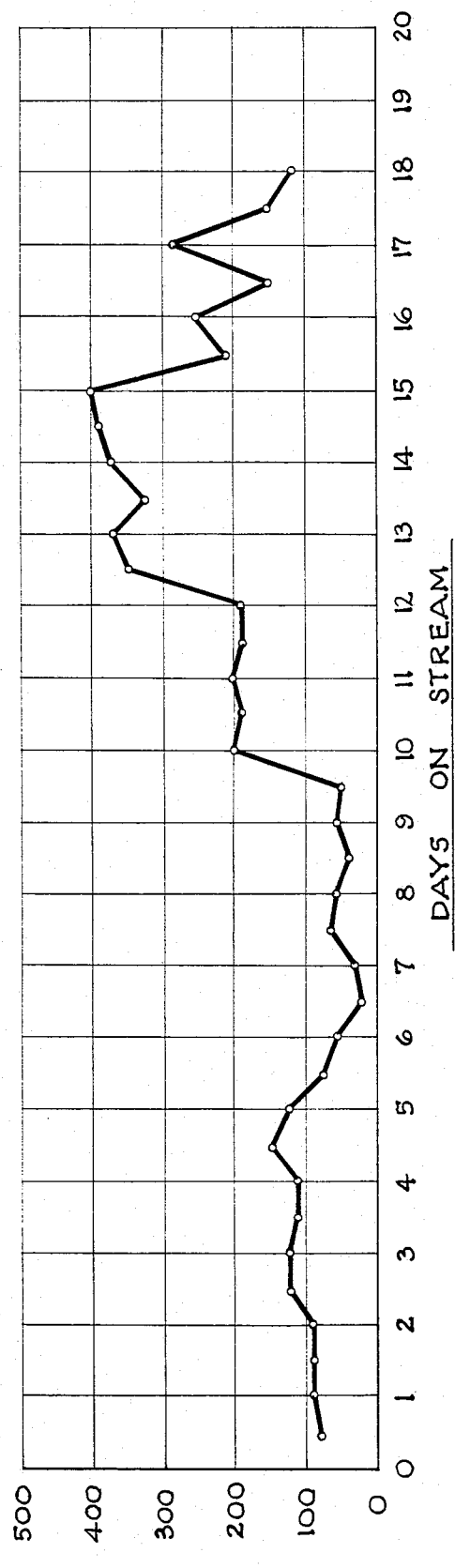
FIGS. 2 and 3 illustrate the same support but onto which has been added, in addition to the copper, the activator metals conventional in the art.
Figure 2:
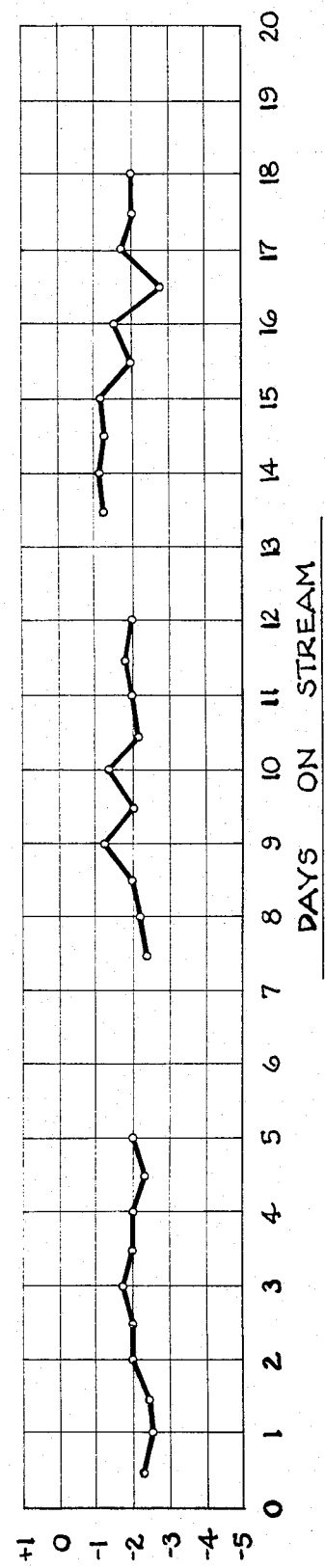
Figure 3:
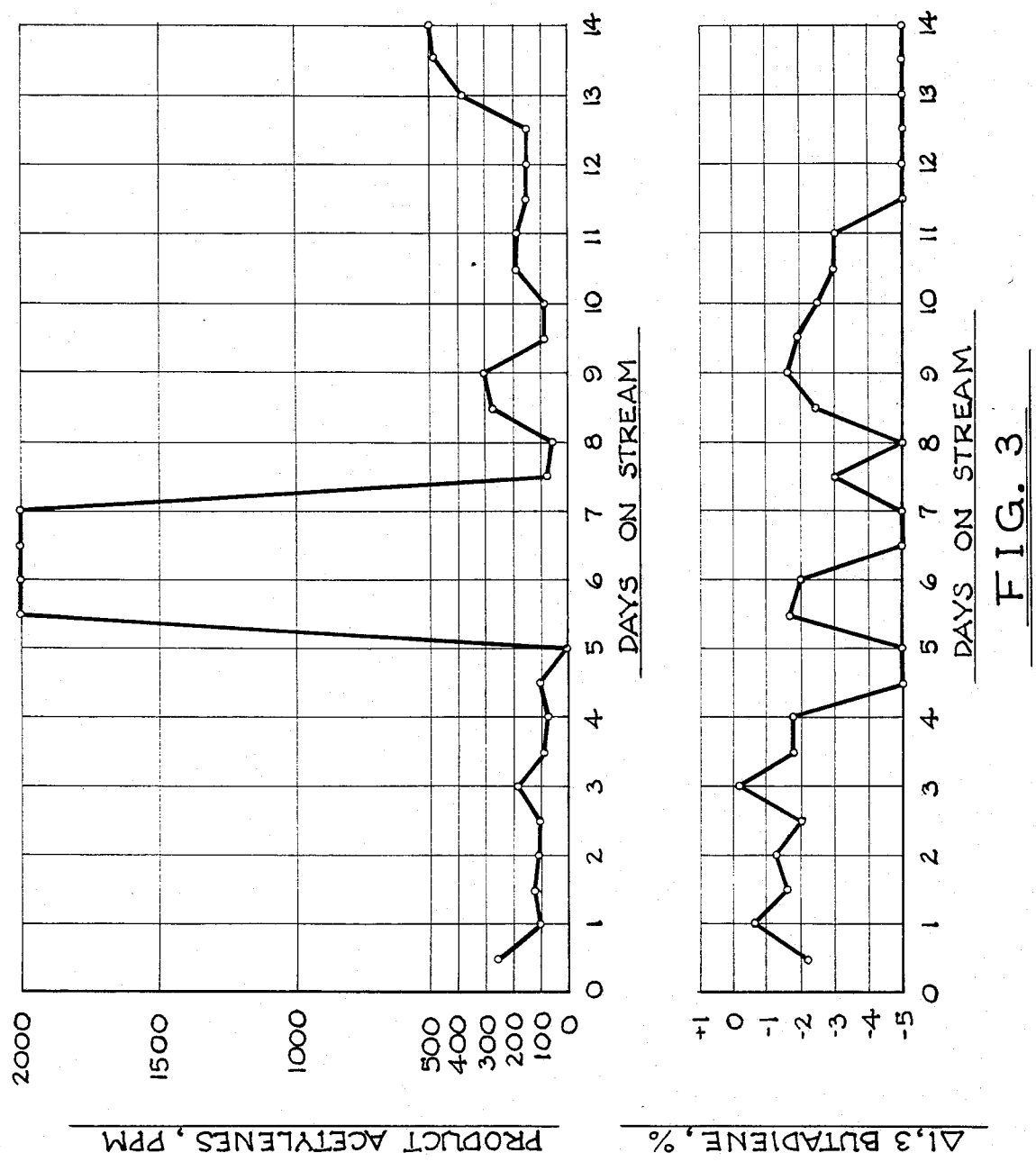
Figure 4:
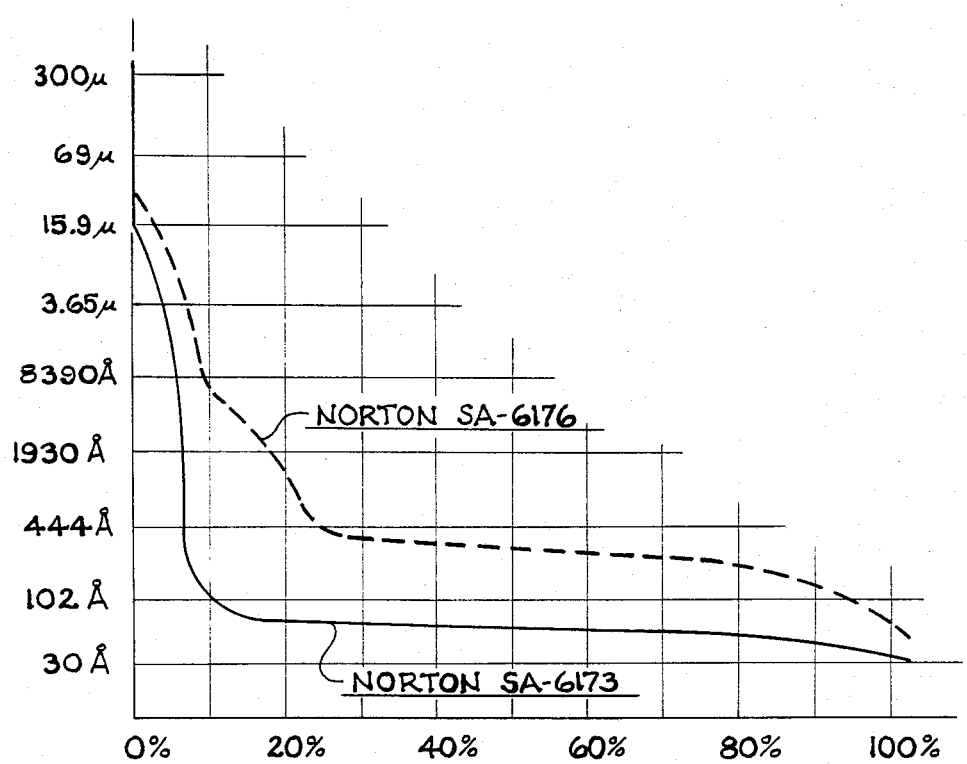
FIGS. 4 and 5 illustrate the pore size distribution of several supports including the SA6173 of the example.
Figure 5:
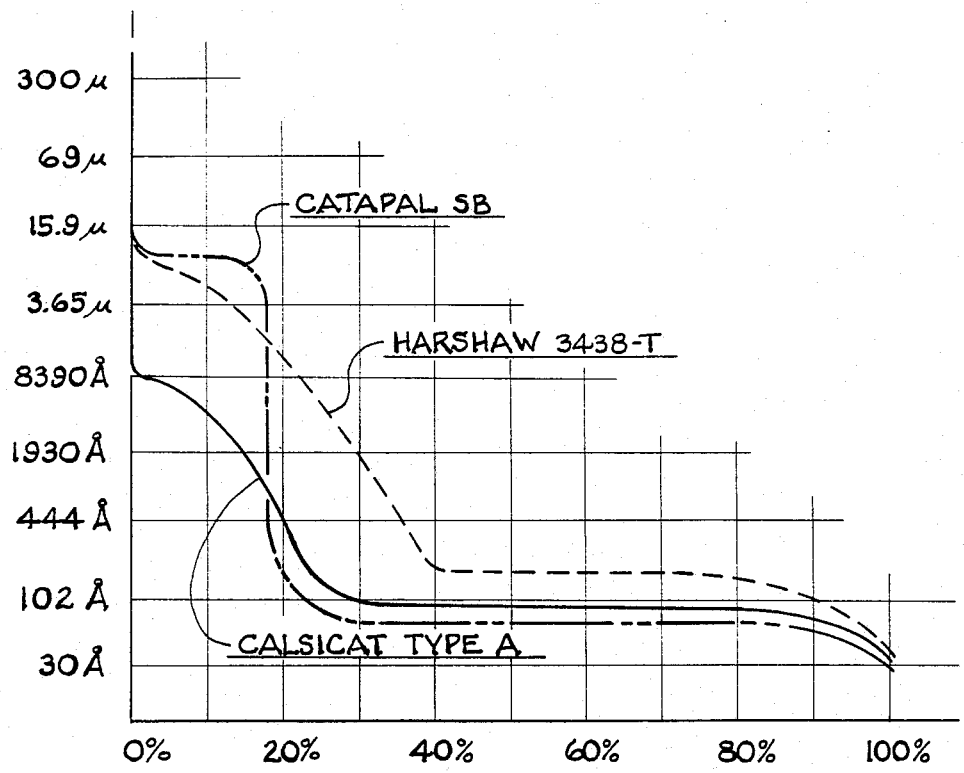

A NORTON SA6173 support was employed to prepare a catalyst and operated for a first cycle of 18 days in a test as afore described. Regeneration occurred on the 18th day. The processed liquids had an average of 200 ppm acetylenes and about a 1% loss in butadiene content on the initial run. The butadiene losses increased from 2 to 4% on the regenerated catalyst over a 15-day second cycle. The graphic daily results are shown in FIGS. 2 and 3.

Example 3 Comparative Example

Figure 6:
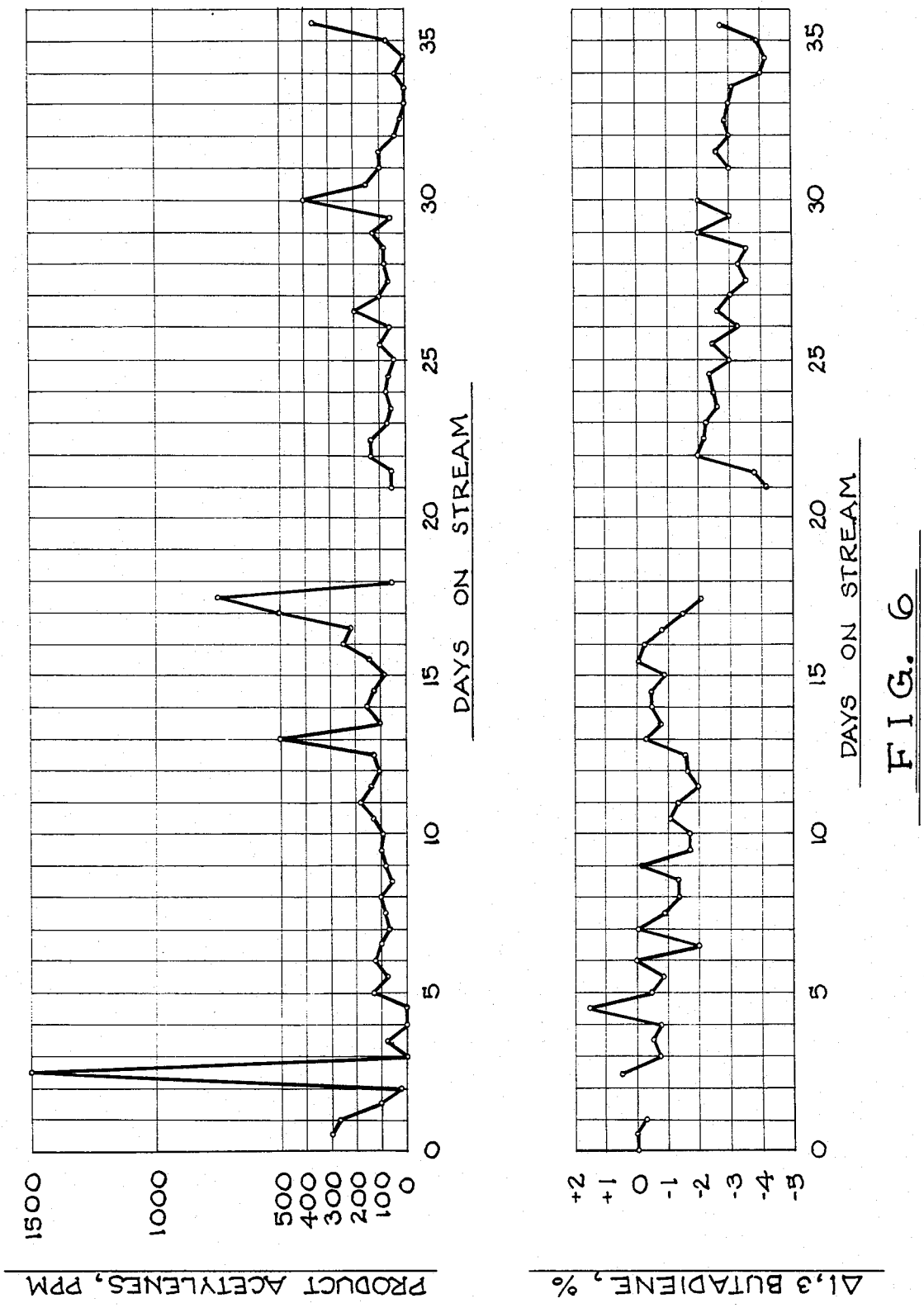
FIGS. 6 and 7 illustrate the results obtained when the heretofore conventional support, $\gamma$-AlOOH, REYNOLDS RA-1 is employed.
Figure 7:
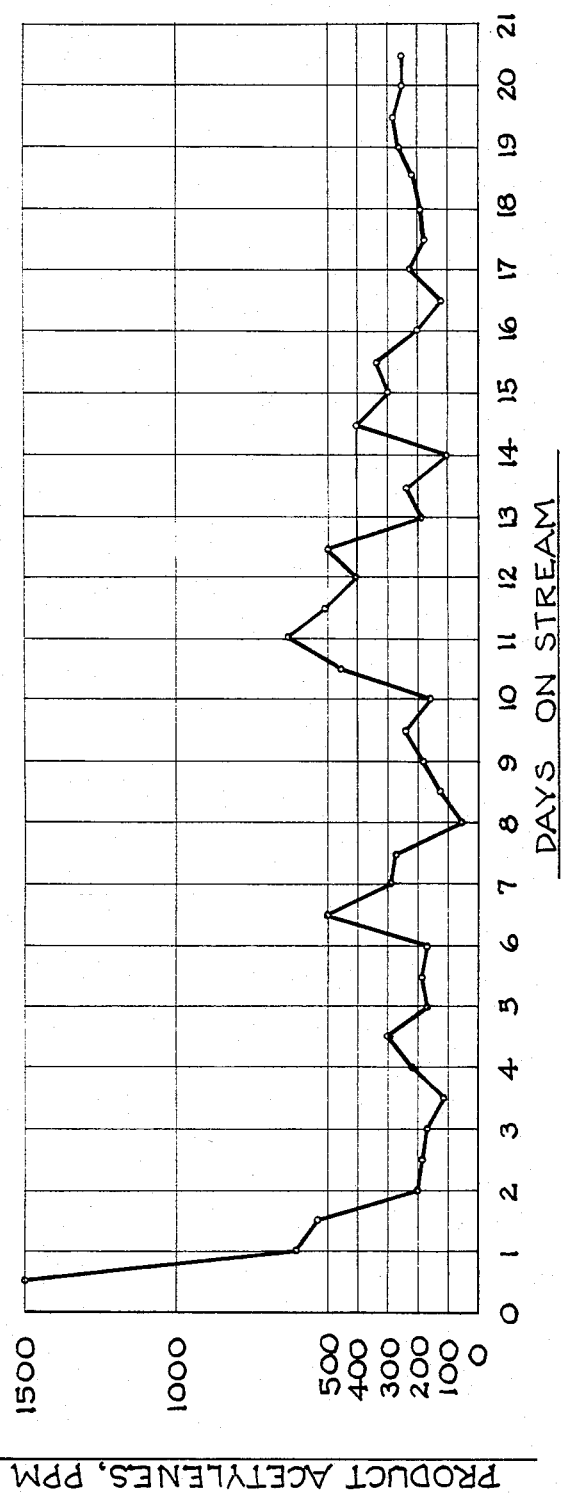

For purposes of comparison, a catalyst having the exact composition as that applied in Example 2 was applied to a conventional gamma alumina (REYNOLDS RA-1 a γ-AlOOH) having a normal sodium content and pore size distribution. The results of this run are illustrated in FIGS. 6 and 7; to wit: 100–200 ppm acetylenes during the first cycle with a loss of butadiene in the 1 to 4% range.

Example 4

Figure 8:
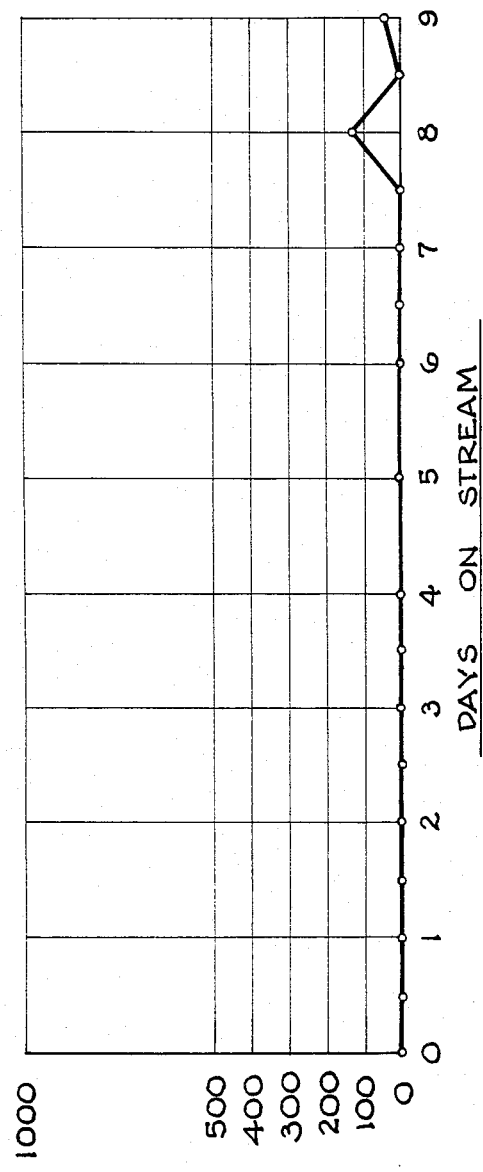
FIGS. 8, 9, 10 illustrate the effect nickel, present in stainless steel, has on the catalyst.
Figure 8:
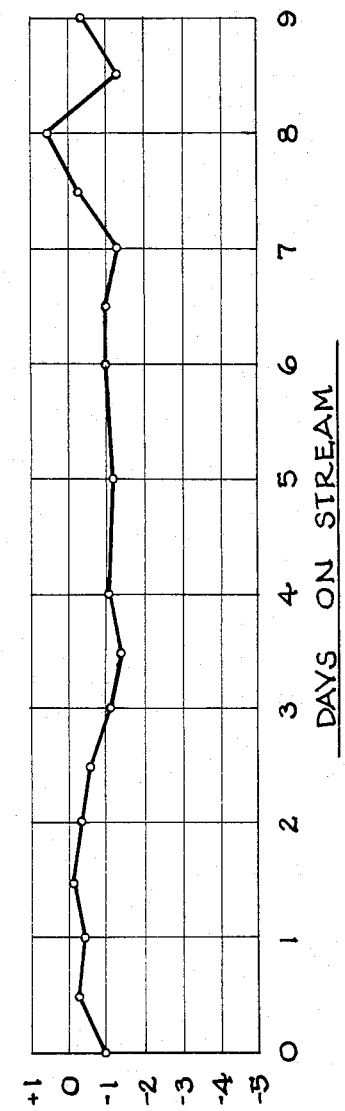
Figure 10:
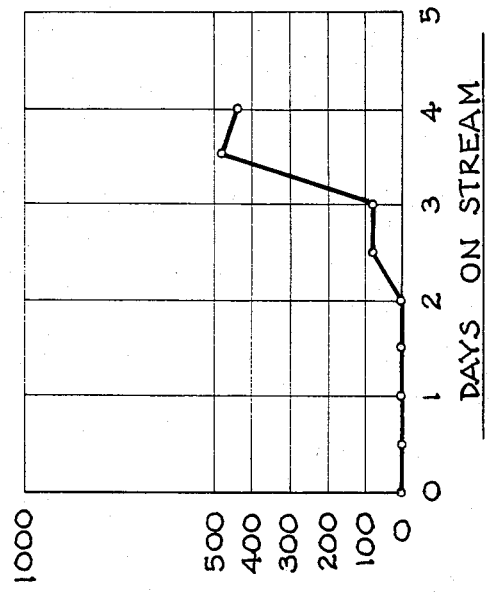
Figure 10:
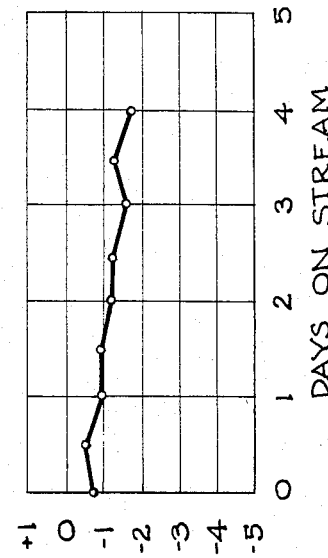
Figure 9:
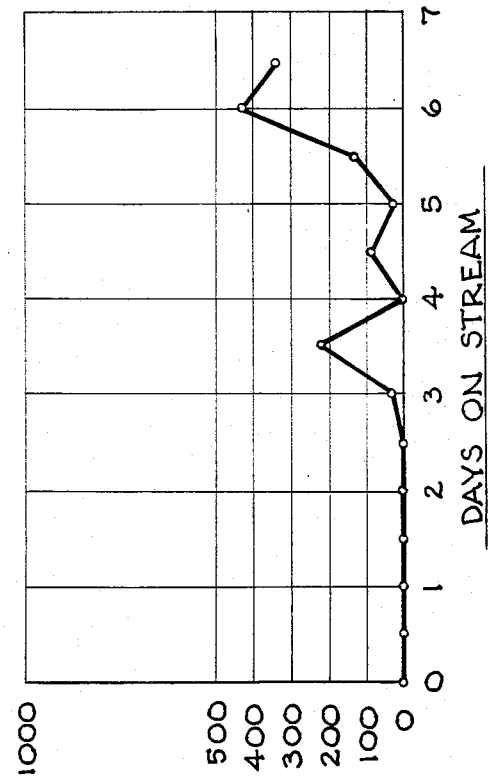
Figure 9:
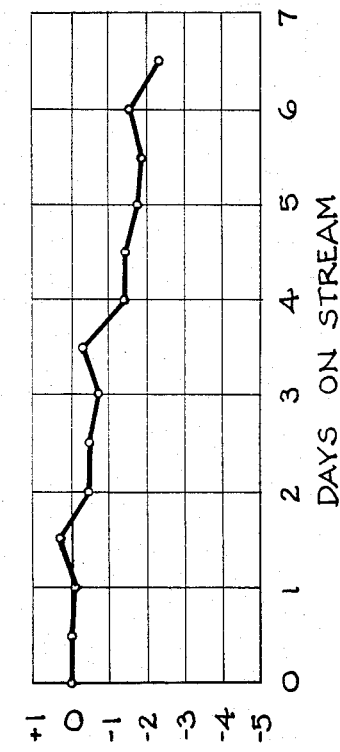

In evaluating the performance of the catalyst and its support in respect to materials of construction, it was found that the materials of construction for the reactor are critical if long, fourteen day, on stream cycles are desired. Thus when one employs a stainless steel containing nickel, the efficiencies of the catalysts of the present invention are somewhat reduced due to the necessity to regenerate the catalyst more often. This phenomenom is overcome when carbon steel is employed as the material of construction for the reactor. The effects of the presence of nickel even though only small amounts are possible at the internal surface of the reactor (wall effect) are clearly seen in FIGS. 8, 9, and 10, the 9th, 12th, and 13th cycles, in a 304 stainless steel reactor. The use of a carbon steel reactor (not containing nickel) results in improved efficiency, i.e. longer run time between regeneration before the acetylenes are no longer effectually hydrogenated. This is shown by comparing results of the three runs, FIGS. 8, 9, and 10, with the results using carbon steel reactors shown in my copending patent application serial no. 473,293 filed Mar. 8, 1983, now U.S. Pat. No. 4,440,956.

I claim:

1. A catalyst for removing α-acetylenes from liquid hydrocarbon streams consisting essentially of finely divided copper metal dispersed on an aluminum oxide support, said support being a gamma alumina as defined by the Joint Committee on Powder Diffraction Standards, #29-63, of high purity having a surface area of between about 68 and about 350 square meters per gram, and 98 to 40 percent of the pores have a pore diameter between about 40Å and 120Å and not more than 25 percent nor less than 2 percent have, a pore diameter between 1000Å to 10,000Å, a silicon content as SiO$_2$ of less than about 0.15 weight %, a sodium content as Na$_2$O of less than about 0.15 weight %, a sulfur content less than about 0.01 weight % and an iron content as Fe$_2$O$_3$ of less than about 0.06 weight %, said gamma alumina may contain up to 35% by weight of alpha alumina.

2. A catalyst for removing α-acetylenes from liquid hydrocarbon streams consisting essentially of a support having thereon finely divided copper metal said support being a substantially high purity gamma alumina as defined by the Joint Committee on Powder Diffraction Standards #29-63, having a surface area of at least about 68 to about 350 square meters per gram, and 98 to 40 percent of the pores have a pore diameter between about 40Å and 120Å and not more than 25 percent nor less than 2 percent have a pore diameter between 1000Å to 10,000Å, and having a sodium content less than about 0.10% and SiO$_2$ being less than 0.15% and which may contain up to 35% by weight of alpha alumina.

3. A catalyst for removing α-acetylenes from liquid hydrocarbon streams consisting essentially of a support having thereon finely divided copper metal said support being a substantially high purity gamma alumina as defined by the Joint Committee on Powder Diffraction Standards #29-63, having a surface area of at least about 68 to about 350 square meters per gram, and 98 to 40 percent of the pores have a pore diameter between about 40Å and 120Å and not more than 25 percent nor less than 2 percent have a pore diameter between 1000Å to 10,000Å, and having a sodium content less than about 0.10% and $SiO_2$ being less than 0.15%, and which may contain up to 35% by weight of alpha alumina, said copper metal being present in from about 3 to 13 weight percent of the support.

* * * * *